United States Patent [19]

Huffman et al.

[11] Patent Number: 4,587,045

[45] Date of Patent: May 6, 1986

[54] INTERMEDIATES FOR PREPARING OCTAPEPTIDE VASOPRESSIN ANTAGONISTS

[75] Inventors: William F. Huffman, Malvern; Michael L. Moore, Media, both of Pa.

[73] Assignee: SmithKline Beckman Corporation, Philadelphia, Pa.

[21] Appl. No.: 734,522

[22] Filed: May 16, 1985

Related U.S. Application Data

[60] Division of Ser. No. 624,542, Jun. 26, 1984, Pat. No. 4,542,124, which is a continuation-in-part of Ser. No. 467,117, Feb. 16, 1983, Pat. No. 4,469,679.

[51] Int. Cl.$^4$ ................................................ C07K 7/06
[52] U.S. Cl. ................................................. 530/328
[58] Field of Search ............................... 260/112.5 R

[56] References Cited

U.S. PATENT DOCUMENTS 4,367,225  1/1983  Manning et al. ............. 260/112.5 R
4,399,125  8/1983  Manning et al. ............. 260/112.5 R Primary Examiner—Delbert R. Phillips
Attorney, Agent, or Firm—Janice E. Williams; William H. Edgerton; Alan D. Lourie

[57] ABSTRACT

Certain octapeptides, which have structures characterized by being a six unit cyclic peptide ring with a dipeptide tail which lacks a glycine unit at position 9, have potent vasopressin antagonist activity. The compounds here claimed are in general characterized by having an amino acid unit at position 4 which is other than valine. An important species of the group is [1-($\beta$-mercapto-$\beta,\beta$-cyclopentamethylenepropionic acid)-2-(O-ethyl-D-tyrosine)-4-$\alpha$-aminobutyric acid-8-arginine-9-desglycine]vasopressin.

5 Claims, No Drawings

INTERMEDIATES FOR PREPARING OCTAPEPTIDE VASOPRESSIN ANTAGONISTS

This is a divisional of Ser. No. 624,542, filed June 26, 1984 and now U.S. Pat. No. 4,542,124, which was, in turn, a continuation-in-part application of Ser. No. 467,117, filed Feb. 16, 1983, now U.S. Pat. No. 4,469,679 issued Sept. 4, 1984.

This invention relates to cyclic octapeptides which are vasopressin antagonists. The compounds of this invention are 9-desGly-vasopressin (VSP) antagonists or 9-desGly-1-Pmp-vasopressins. More specifically, the structures of these octapeptides have a β-mercapto-β,β-cycloalkylenepropionic acid and five amino acid units cyclized into a 6-unit ring by means of a sulfur derived from a cysteine unit and a sulfur from the propionic acid unit. The ring also has a distinguishing dipeptide tail, which lacks a glycine unit, attached by means of an amido linkage to the 6-cysteine unit.

BACKGROUND OF THE INVENTION

M. Manning, W. H. Sawyer and coworkers have published a series of publications describing various [1-(β-mercapto-β,β-cyclopentamethylenepropionic acid)-4-valine]-arginine-vasopressin congeners which have antivasopressin activity. Representative of these are EPA No. 61,356, U.S. Pat. No. 4,367,225 and U.S. Pat. No. 4,399,125.

All of the Manning compounds have a tripeptide chain attached at unit 6 and are, of course, nonapeptides. The present compounds are distinguished over these by being octapeptides, by having a des-Gly dipeptide tail attached at unit 6 and by having potent vasopressin antagonist activity.

The potent biological activity of the compounds of the present invention is unexpected in view of the fact that des-glycinamide[9]-vasopressin and des-lysine[8]-desglycinamide[9]-vasopressin [T. Barth et al., Collection Czechoslov. Chem. Commun. 39, 506 (1974)] as well as desglycine[9]-oxytocin [B. Berde et al., Handb. Exp. Pharm 23 860 (1968)] retain little of the activity of their respective parent compounds. In fact, Barth reports that desglycinamide[9]-AVP has CNS activity but practically no antidiuretic or uterotonic activity, Belgian Pat. No. 896,509.

Certain of the peptide art designations used in the specification and claims are the following: Cap, β-mercapto-β,β-cycloalkylenepropionic acid; Pmp, β-mercapto-β,β-cyclopentamethylenepropionic acid; Chg, cyclohexylglycine; Abu, α-amino-n-butyric acid; Cha, cyclohexylalanine; Pba, aminophenylbutyric acid; Gln, glutamine; Gly, glycine; Tyr, tyrosine; Phe, phenylalanine; Phe(4'-Alk), lower alkylphenylalanine; Val, valine; Nva, norvaline; Ile, isoleucine; Nle, norleucine; D-aIle, D-allo-isoleucine; Leu, leucine; Ala, alanine; Lys, lysine; Arg, arginine; Asn, asparagine; Met, methionine; Tos, tosylate; HF, hydrogen fluoride; BHA, benzhydrylamine; DIEA, diisopropylethylamine; 4-MeBzl, 4-methylbenzyl; TFA, trifluoroacetic acid; DCC, dicyclohexylcarbodiimide; HBT, 1-hydroxybenzotriazole; ADH, antidiuretic hormone; ACM, acetamidomethyl; DMAP, dimethylaminopyridine.

When the term "vasopressin" is used, in the specification only, it means L-arginine vasopressin (AVP) unless otherwise modified. The AVP derivatives of this invention are preferred. "Alk" represents a lower alkyl of 1-4 carbons which is optionally attached to the nitrogen at Y, to the oxygen substituent of the tyrosine unit when such is present at position 2 or to the phenyl ring of a phenylalanine unit at ring position 3. Such alkyl substituents include methyl, ethyl, n-propyl, isopropyl or butyl.

Therefore, in the description herein and in the claims, the nomenclature common in the art of peptide and vasopressin chemistry is used. When no configuration is noted, the amino acid unit is in the L, or naturally occurring, form.

DESCRIPTION OF THE INVENTION

The desGly[9] compounds of the invention are illustrated by the following structural formula:

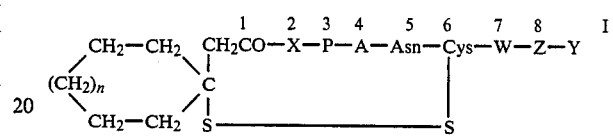

in which:
P is Phe or Phe(4'-Alk);
X is D-Phe, D-Val, D-Nva, D-Leu, D-Ile, D-aIle, D-Pba, D-Nle, D-Cha, D-Abu, D-Met, D-Chg, D or L-Tyr or D or L-Tyr(alk);
Y is $NH_2$, NHAlk, NHBzl or OH;
W is D-Pro, L-Pro or ΔPro (dehydro-Pro);
A is Val, Ile, Abu, Ala, Gly, Lys, Cha, Nle, Phe, Leu, Chg or Nva;
Z is D-Arg, L-Arg, D-Lys or L-Lys;
n is 0, 1 or 2, or a pharmaceutically acceptable salt, ester prodrug or complex thereof.

A subgeneric group of compounds of this invention comprises compounds of formula I in which X is D-Tyr, D-Cha, D-Phe, D-Ile, D-Leu, D-Val or D-Tyr(Et); P is Phe or Phe(4'-Et), A is as defined above, Y is $NH_2$; W is Pro, Z is Arg and n is 1.

The compounds of formula I in which X is D-Tyr(Et) are particularly active ADH antagonists as are the amide[8] congeners.

Individual compounds of interest are [1-(β-mercapto-β,β-cyclopentamethylenepropionic acid)-2-D-tyrosine-4-valine-8-arginine-9-desglycine]vasopressin, [1-(β-mercapto-β,β-cyclopentamethylenepropionic acid)-2-D-tyrosine-4-valine-8-arginine-9-desglycinamide]vasopressin and, especially, [1-(β-mercapto-β,β-cyclopentamethylenepropionic acid)-2-(O-ethyl-D-tyrosine)-4-valine-8-arginine-9-desglycine]vasopressin.

Also included in this invention are various derivatives of the compounds of formula I such as addition salts, prodrugs in ester or amide form and complexes. The addition salts may be either salts with pharmaceutically acceptable cations such as $NH_4^{\oplus}$, $Ca^{++}$, $K^{\oplus}$ or $Na^{\oplus}$ at the terminal acid group (Y=OH) or with a pharmaceutically acceptable salt at a basic center of the peptide (as in the Arg units). The acetate salt forms are especially useful although hydrochloride, hydrobromide and salts with other strong acids are useful. The compounds, also, form inner salts or zwitter ions as when Y is OH. The ester prodrug forms are, for example, lower alkyl esters of the acids of formula I which have from 1-8 carbons in the alkyl radical or aralkyl esters such as various benzyl esters. Other latentiated derivatives of the compounds of formula I will be obvious to those skilled in the art "Complexes" include various solvates such as hydrates or alcoholates or those with supporting resins, such as a Merrified resin.

The compounds of formula I are prepared by cyclizing a linear octapeptide by means of the two mercapto groups, at the cysteine unit (Cys) at position 6 and at the β-mercapto-β,β-cycloalkylenepropionic acid unit (Cap) at position 1. The cyclization reaction occurs readily in the presence of a mild oxidizing agent capable of oxidizing a mercaptan to a disulfide. The reaction is represented as follows:

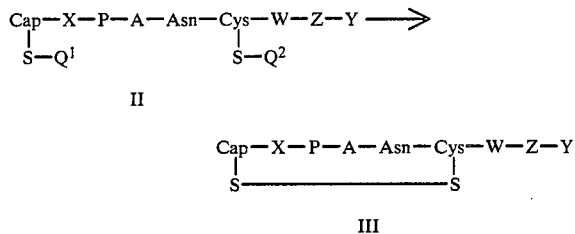

in which:

X, P, A and Y are as defined for formula I, above;

Z is as defined for formula I above or also may be a single bond whenever Y is OH;

W is as defined for formula I above or also may be OH whenever Z and Y are absent; and $Q^1$ and $Q^2$ are, each, hydrogen or a displaceable group.

The intermediates of formula II are new compounds and are a part of this invention. The compounds of formula III in which either or both W and Z are absent are also new compounds useful as intermediates as described below. The latter have VSP antagonist activity at a lower level than that of the octapeptides.

The cyclization reaction of this reaction sequence is most usefully carried out by oxidation. Any oxidizing agent known to the art to be capable of converting a dimercaptan to a disulfide may be used. Exemplary of such agents are an alkali metal ferricyanide, especially potassium or sodium ferricyanide, oxygen gas, diiodomethane or iodine.

As an example, potassium ferricyanide is added to the dimercaptan of formula II dissolved in a suitable inert solvent, for example, water or aqueous methanol at temperatures of from 0°–40°. Often, oxidation is at a pH of 7–7.5 at ambient temperature in dilute solution gives good yields, 40–50%, of the cyclic compound.

The compounds of formula III which are the Cys-(OH)$^6$ or Pro(OH)$^7$ compounds are reacted with a dipeptide, a protected (NH$_2$)-WZY, or an amino acid, (NH$_2$)-Z-Y, respectively, as described hereafter.

The linear mercaptan starting material may or may not have displaceable or protective groups common to the art ($Q^1$ and $Q^2$) present at the various amino acid units. Such protective groups include benzyl, p-methoxybenzyl, 1-adamantyl, t-butyl, p-nitrobenzyl, trityl, benzylthiomethyl, ethylcarbamoyl or acetamidomethyl. Benzyl, adamantyl or t-butyl are removed by mercuric (halo) acetate salts in aqueous methanol at 0°–80°. The protective group is usually removed before cyclization such as during the hydrogen fluoride splitting of the peptide from the supporting resin. It may, however, be removed either during the cyclization or, in situ, before cyclization.

The S-acetamidomethyl groups are especially useful. For example, S-ACM-Pmp-D-Tyr(Et)-Phe-Val-Asn-S-ACM-Cys-Pro-OBzl was treated with potassium carbonate in aqueous methanol to give the Pro acid linear peptide in 78–84% yield. This was, then, oxidatively cyclized using iodine in aqueous methanol to give the desired Pro(OH)$^7$ product in 65–70% yield. Alternatively, the protected product was cyclized under the same conditions with initial iodine treatment followed by potassium carbonate removal of the protective ester radical. The Pro$^7$ acid was, then, condensed with Arg(NH$_2$), using DCC and DMAP in DMF at 0°–20° to give the

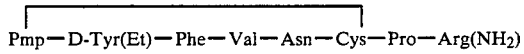

in 45% yield.

Iodine, therefore, removes the S-protective group, especially the ACM group, and cyclizes the intermediate. Mercuric acetate or lead acetate also remove the ACM group to yield a metal mercaptide. This is converted to the thiol in situ by treatment with hydrogen sulfide and, then, oxidized in a separate step.

The desired cyclic octapeptide of formula I can be conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel prepared by cross-linking dextran with epichlorohydrin.

As an alternative to the cyclization of the linear intermediates of formula II suggested above, the cyclized 6-Cys acids or 7-Pro acids (those of formula I in which either both tail units, W and Z, or only one tail unit, Z, are absent) are condensed with a protected dipeptide, W-Z-Y, or with an amino acid, Z-Y, respectively. The reaction of the Cys acid or the Pro acid with a suitably protected dipeptide or amino acid is carried out using any amide forming reaction common to the peptide art. Usually, substantially equimolar quantities of the starting materials are reacted in the presence of a carbodiimide, such as dicyclohexylcarbodiimide, plus 1-hydroxybenzotriazole or dimethylaminopyridine in an organic solvent at from 0°–35°, preferably, from ice to room temperature. The protective groups are removed by a reaction which will not split the disulfide bond of the hexapeptide ring, for example, mild alkali.

The important intermediates of formula II are conveniently prepared using solid-phase methods of peptide synthesis as discussed in M. Manning et al., J. Med. Chem. 25 46 (1982). A commercial benzhydrylamine support resin (BHR) is used to prepare the end products of formula I in which Y is NH$_2$ (the des-glycines) and a chloromethyl support resin (CMR) is used to prepare the compounds of formula I in which Y is OH (the des-glycinamides).

The peptide chain of the linear peptides of formula II is build up, stepwise, proceeding from unit 8 working toward unit 1. Each unit is properly protected as known in the peptide art and as described below. Alternatively, various oligopeptides may be built up using liquid or support reactions, then condensed as a last step in the reaction sequence for preparing the dimercapto intermediates.

The preferred sequence of resin supported step reactions is conveniently carried out in a Beckman 990B peptide synthesizer without isolation of each intermediate peptide. The details of the procedure are in the working examples presented hereinafter. Solution or enzyme reaction conditions are applicable here as known to the art.

The various amino acids, which are consecutively added to the resin supported chain are protected as known to the art. For example, the Boc protecting group is used for an amino group especially at the α-position; an optionally substituted benzyl, for the mercapto groups at the Pmp and Cys units; tosyl, for the Arg unit; and an optionally substituted carbobenzoxy(Z) for the Tyr or Lys units. The protective groups should, most conveniently, be those which are easily removed, that is, using acid treatment for the tert.-butyloxycarbonyl group, sodium-liquid ammonia or catalytic hydrogenation for the benzyl or carbobenzoxy groups where the removal reaction conditions are not conducive to reaction at other portions of the peptide such as the disulfide bond.

As other examples of protecting groups, the amino group of an amino acid or oligopeptide is protected conventionally by an acyl group such as formyl, trifluoroacetyl, phthaloyl, p-toluenesulfonyl or o-nitrophenylsulfonyl group; a benzyloxycarbonyl group such as benzyloxycarbonyl, o-bromobenzyloxycarbonyl, p-bromobenzyloxycarbonyl, o- or p-chlorobenzyloxycarbonyl, p-nitrobenzyloxycarbonyl or p-methoxybenzyloxycarbonyl, an aliphatic oxycarbonyl group such as trichloroethyloxycarbonyl, t-amyloxycarbonyl, t-butoxycarbonyl or diisopropylmethoxycarbonyl, or an aralkyloxycarbonyl group such as 2-phenylisopropoxycarbonyl, 2-tolylisopropoxycarbonyl or 2-p-diphenylisopropoxycarbonyl. Amino groups are also protected by forming enamines by reaction with a 1,3-diketone such as benzoylacetone or acetylacetone.

The carboxyl groups can be protected by amide formation, hydrazide formation or esterification. The amide group is substituted, if necessary, with a 3,4-dimethoxybenzyl or bis-(p-methoxyphenyl)-methyl group. The hydrazide group is substituted with a benzyloxycarbonyl, trichloroethyloxycarbonyl, trifluoroacetyl, t-butoxycarbonyl, trityl or 2-p-diphenyl-isopropoxycarbonyl group. The ester group is substituted with an alkanol such as methanol, ethanol, t-butanol or cyanomethylalcohol; an aralkanol such as benzylalcohol, p-bromobenzylalcohol, p-chlorobenzylalcohol, p-methoxybenzylalcohol, p-nitrobenzylalcohol, 2,6-dichlorobenzylalcohol, benzhydrylalcohol, benzoylmethylalcohol, p-bromobenzoylmethylalcohol or p-chlorobenzoylmethylalcohol; a phenol such a 2,4,6-trichlorophenol, 2,4,5-trichlorophenol, pentachlorophenol, p-nitrophenol or 2,4-dinitrophenol; or a thiophenol such as thiophenol or p-nitrothiophenol. The hydroxy group in tyrosine is optionally protected by esterification or etherification. A group protected by esterification is, for example, an O-acetyl group; a O-benzoyl group, O-benzyloxycarbonyl or O-ethyloxycarbonyl. A group protected by etherification is, for example, an O-benzyl, O-tetrahydropyranyl or O-t-butyl group.

The amino group in the guanidino group in arginine can be protected by a salt forming, nitro, tosyl, benzyloxycarbonyl or mesitylene-2-sulfonyl group. However, it is not always necessary to protect the guanidino group.

The protected linear peptide intermediate is split from the carrying resin matrix, for example, by using ammonia in an alcoholic solvent, and, then, is treated to remove the protective groups, such as by using sodium-liquid ammonia. This procedure gives the amide derivative of the linear octapeptide.

More conveniently, the two steps are combined by treating the resin supported peptide with anhydrous hydrogen fluoride in the presence of a suitable cation scavenger as known to the art, such as anisole, to give the octapeptide intermediate of formula II, in dimercaptan form, and in good yield.

The compounds of this invention have potent vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. We believe the mechanism of action is at the vasopressin receptors ($V_2$-receptors) located on the plasma membrane of certain renal epithelial cells. The most notable pharmocodynamic effect of the ADH antagonists of the invention is that of a water diuretic rather than of a natriuretic such as a thiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, congestive heart failure or a component of any traumatic condition resulting from serious injury or disease in which the agonism of naturally occurring vasopressin at the VSP-mediated receptor sites is a contributing factor.

The second group of vasopressin receptor sites are the vascular pressor sites ($V_1$-receptors) located within the cardiovascular system itself. For example, Compound 5 of Table I below was tested in the Dyckes protocol (U.S. Pat. No. 4,367,255) for inhibition of vasopressin-induced vasoconstriction in the rat; in vitro ($pA_2$ 8.40) and in vivo ($pA_2$ 7.71). Antagonism at the $V_2$ receptor sites results in vasodilation with an end result of anti-hypertensive activity. Treatment of dysmenorrhea is another utility for the compounds of this invention when administered intravenously or intranasally.

The compounds of this invention, therefore, are used to treat edema or to expell water in patients in need of such treatment by administering parenterally or by insufflation a nontoxic but effective quantity of the chosen compound, preferably combined with a pharmaceutical carrier. Dosage units of the active ingredient are selected from the range 0.01 to 10 mg/kg, preferably 0.01 to 5 mg/kg, based on a 70 kg patient. The dosage units are applied from 1 to 5 times daily.

The pharmaceutical composition for inducing vasopressin antagonism contains an active ingredient of formula I in the form of a dosage unit as described above dissolved or suspended in a standard liquid carrier. A standard carrier is isotonic saline, contained in an ampoule or a multiple dose vial which is suitable for parenteral injection such as for intravenous, subcutaneous or intramuscular administration. A composition for insufflation is similar but is usually administered in a metered dose applicator or inhaler. Pulverized powder compositions may, also, be used, along with oily preparations, gels, buffers for isotonic preparations, emulsions or aerosols, as standard composition forms.

The compounds of this invention have been demonstrated to have unique antagonistic activity toward the natural antidiuretic hormone (anti-ADH activity), in vitro, in the medullary tissue of hog or human kidney and, in vivo, in the hydropenic rat or the hydropenic monkey. Details of the in vitro protocols are in F. L. Stassen et al., J. of Pharm. Exp. Ther. 233, 50-54 (1982) but the calculations of cyclase activity and binding potential at the receptor site are as follows:

Test Procedure for Assay of Adenylate Cyclase Activity:

In each experiment the amount of $^{32}P/cAMP$ formed in the absence of medullary membrane is determined (blank). The blank value is subtracted from all experimental data. The compound is tested for its effect on basal adenylate cyclase activity and/or on vasopressin stimulated activity. Each determination is carried out in triplicate. The Ka value is derived from a Lineweaver-Burke plot. Rel. $V_{max} = (V_{max}drug/V_{max}$ vasopressin$)\times 100$. $K_i = I/[(Ka'/Ka) - 1]$ where I is the concentration of the antagonist, and Ka' and Ka are the concentrations of vasopressin required to give half-maximal activity of adenylate cyclase in the presence and absence of antagonist, respectively.

Test Procedure for Binding Assay:

In each experiment, the amount of $^3H$-vasopressin bound in the absence and in the presence of an excess of vasopressin ($7.5 \times 10^{-6}M$) is measured in triplicate. These values represent total and non-specific binding, respectively. The $K_B$ of a compound is derived from the equation for competitive inhibition: $K_B = IC_{50}/(1 + L/K_D)$, where $IC_{50}$ is the concentration required for 50% inhibition of specific $^3H$-vasopressin binding, L is the concentration of the ligand, and $K_D$ is the dissociation constant of $^3H$-vasopressin ($K_D = 3.6 \times 10^{-9}M$; 1 SD=$0.4 \times 10^{-9}M$). This is the average $K_D$ value determined on 3 preparations of hog kidney membranes.

Hydropenic Rat Protocol

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEq/rat electrolyte excreted, mg/rat urea excreted, and osmolality in milli-Osmoles/kg H$_2$O. A tolerance test is used to determine significance. ED$_{300}$ is defined as the dose of compound ($\mu$g/kg) required to lower urine osmolality to 300 m-Osmoles/kg. ED$_{500}$ is defined as the dose of compound ($\mu$g/kg) required to lower urine osmolality to 500 m-Osmoles/kg. The hydropenic monkey protocol is similar.

TABLE I

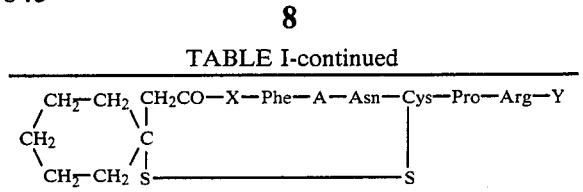

| | | | anti-ADH activity | | |
| | | | in vivo (Rat) ED$_{300}$ | in vitro (Pig) | |
| X | Y | A | ($\mu$g/kg)* | Ki(nM) | K$_B$(uM) |
|---|---|---|---|---|---|
| 1. D-Tyr | Gly—NH$_2$ | Val | 32 | 30 | 0.082 |
| 2. D-Tyr | NH$_2$ | Val | 63 | 27 | 0.065 |
| 3. D-Tyr | OH | Val | 156 | 160 | 0.35 |
| 4. D-Tyr(Et) | Gly—NH$_2$ | Val | 9.9 | 5.9 | 0.011 |
| 5. D-Tyr(Et) | NH$_2$ | Val | 5.8 | 3.0 | 0.0078 |
| 6. D-Tyr(Et) | NH$_2$ | Abu | 13 | 7.6 | 0.018 |

*Estimated dose of peptide delivered ip stat ($\mu$g/kg) which results in a reduction of U$_{osm}$ from hydropenic levels to 300 m-Osmoles/kg H$_2$O.

Table I demonstrates, in the described protocols, the anti-vasopressin activity of selected representative compounds whose octapeptide structures have the desGly dipeptide tail which is characteristic of the compounds of this invention. Presence of substantial antagonistic activity is unexpected because, in the agonist series, the des-Gly-oxytocin has an opposite effect on blood prssure compared with oxytocin itself (See B. Berde et al., loc. cit.) and shortening the linear tail of oxytocin and vasopressin result is known in the art to cause "a striking decrease of the typical biological activities of the substances" (see T. Barth et al., loc. cit.).

Compound 5 of Table I, furthermore, has proven to be a compound of exceptional antagonist activity across the various testing protocols in hog or human tissue in vitro tests as well as in hydropenic rat and monkey tests. Its anti-ADH activity, manifested as the dose required to decrease urine osmolality to 300M Osm/kg water in the conscious hydropenic squirrel monkey test, is ED$_{300}$=8.6 Nmoles/kg (i.e.). That of Compound 4 of Table I is 33.1 Nmoles/kg. The 2-D-Phe analog of the latter compound is 319.0 Nmoles/kg.

The following examples are intended solely to teach the preparation of the compounds of this invention. All temperatures are in degrees Centigrade.

EXAMPLE 1

Solid-Phase Synthesis of Pmp(Bzl)-D-Tyr(Br-Z)-Phe-Val-Asn-Cys(OMe-Bzl)-Pro-Arg(Tos) resin For the solid-phase synthesis of the titled resin supported peptide, Boc-Arg(Tos) resin (3 mmol/5.4 grams of resin) was used as starting material. The appropriately protected amino acids were coupled sequentially onto the Boc-Arg(Tos) resin, prepared by reacting Boc-Arg(Tos) as the cesium salt with commercial Merrifield resin (Cl-CH$_2$ resin) as known to the art, by using a manual program as described in the following steps:

1. washed with methylene chloride (3 times, 1 minute).
2. prewashed with 33% trifluoroacetic acid in methylene chloride with 1% indole (1 time, 1 minute).
3. deprotection with 33% trifluoroacetic acid in methylene chloride with 1% indole (20 minutes).
4. washed with methylene chloride (3 times, 1 minute).
5. prewashed with 10% triethylamine in methylene chloride (1 time, 1 minute).
6. neutralization with 10% triethylamine in methylene chloride (10 minutes).
7. washed with methylene chloride (3 times, 1 minute).

8. protected amino acid (10 mmol) in triethylamine in methylene chloride and 0.5M N,N'-dicyclohexylcarbodiimide in methylene chloride (20 ml) were added.

The reaction time was up to two hours.

In the case of the coupling of the Asn moiety, 1-hydroxybenzotriazole (HBT, 10 mmol) was added with Boc-Asn in dry dimethylformamide. Dry dimethylformamide (DMF) was also used as solvent when Pmp(Bzl) was coupled onto the peptide resin, using 4-dimethylaminopyridine (10 mM). Completion of each coupling reaction was monitored by the ninhydrin test. The 4-methoxybenzyl group was used to protect the thiol group of Cys and the 2-bromo-carbobenzoxy group was employed to block the phenolic hydroxyl of D-Tyr.

The resulting protected Pmp(Bzl)-D-Tyr(Br-Z)-Phe-Val-Asn-Cys(OMe-Bzl)-Pro-Arg(Tos)-resin was washed well with methylene chloride and methanol, respectively. After drying in vacuo overnight, 8.4 grams of the titled protected resin intermediate was collected.

Preparation of

Pmp—D-Tyr—Phe—Val—Asn—Cys—Pro—Arg—NH$_2$

Pmp(Bzl)-D-Tyr-(p-bromocarbobenzoxy)-Phe-Val-Asn-Cys(OMe-Bzl)-Pro-Arg(Tos) resin (4 g, ca. 1.5 mmol) was subjected to ammonolysis using saturated ammonia/methanol solution (200 ml) in dry dimethylformamide (50 ml) at room temperature for 48 hours. After evaporation to dryness, the residue was precipitated by ethyl acetate/n-hexane and filtered to give the protected octapeptide amide (1.54 g).

This crude peptide was dissolved in liquid ammonia (250 ml) and treated with sodium/liquid ammonia solution to give Pmp-D-Tyr-Phe-Val-Asn-Cys-Pro-Arg-NH$_2$ which was, then, oxidized using 0.01M potassium ferricyanide solution in 4 l. of aqueous solution at pH 7-7.5. After the completion of oxidation reaction, the pH of aqueous solution was adjusted to pH 4.5 by adding glacial acetic acid. This solution was passed through a weakly acid acrylic resin (Bio-Rex 70) column (11×2.5 cm, H+ form) slowly. The column was eluted with 5% and 50% acetic acid solution, respectively. Crude cyclized

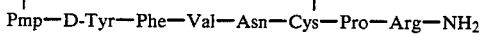
Pmp—D-Tyr—Phe—Val—Asn—Cys—Pro—Arg—NH$_2$ was collected from 50% acetic acid solution fractions (860 mg).

Purification of

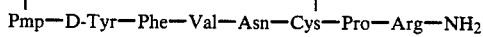
Pmp—D-Tyr—Phe—Val—Asn—Cys—Pro—Arg—NH$_2$

1. Counter-current distribution:
    Sample: 860 mg crude, n-BuOH/HOAc/H$_2$O (4:1:5) 250 transfers
    (a) fr. 186-204,  436 mg
    (b) fr. 182-185 & 205-218,  219 mg
2. Partition chromatography:
    Sample: 250 mg (from 1-a),  G-25 fine (2.5 × 55 cm),
    n-BuOH/HOAc/H$_2$O (4:1:5)

Purification of

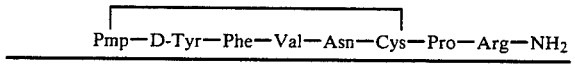
Pmp—D-Tyr—Phe—Val—Asn—Cys—Pro—Arg—NH$_2$ (a) fr. 32-46   222 mg
3. Preparative HPLC:
    Sample: 40 mg (from 2-a); Alltech C18, 3000 psig. Flow rate: 3.0 ml/min.
        Buffer A: 0.1% TFA
        Buffer B: 0.25% TFA/CH$_3$CN (4:6)
        60% B; isocratic; 235 nm (2.0 AUFS)
        Injection: 10 mg/0.5 ml. buffer A
    17 mg of pure titled compound.
4. Ion-exchange Chromatography:
    Sample: 365 mg (from 1-a & 2-a); CMC; 0.01M NH$_4$OAc to 0.1M NH$_4$OAc
                                    Linear gradient
    (a) fr. 51-70     93.5 mg
    (b) fr. 71-89     86.5 mg
    (c) fr. 91-110    65   mg
    (d) fr. 111-121   24.5 mg

EXAMPLE 2

Preparation of Pmp—D-Tyr—Phe—Val—Asn—Cys—Pro—Arg

Pmp(Bzl)-D-Tyr(Br-Z)-Phe-Val-Asn-Cys(OMe-Bzl)-Pro-Arg(Tos)-Resin (4.2 g, 1.5 mmol) from Example 1, in 4.5 ml distilled anisole, was reacted with anhydrous hydrogen fluoride (40 ml) at 0° for one hour. After treatment as described above and evaporation in vacuo to dryness, the residue was treated with anhydrous ether and filtered off to give 1.33 g crude peptide. The completion of removal of the Bzl group from the Pmp moiety was carried out using the sodium in liquid ammonia reaction as described in Example 1. The resulting unprotected octapeptide was cyclized using 0.01M potassium ferricyanide solution at pH 7-7.5 until color persisted for 30 minutes again as described above in the preparation of the amide.

Desglycinamide octapeptide (600 mg) was collected after acidifying the oxidation solution with acetic acid to pH 4.5 and passing the reaction mixture over a Bio-Rex-70 column with 1 l. of 5% acetic acid as eluent.

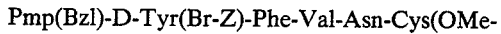
Purification of Pmp—D-Tyr—Phe—Val—Asn—Cys—Pro—Arg

1. Counter-current distribution:
    Sample: 600 mg from Bio-rex 70. n-BuOH/HOAc/H$_2$O (4:1:5); 200 transfers
    (a) fr. 150-161           169 mg
    (b) fr. 133-149 & 162-163
2. Preparative HPLC:
    Sample: 52 mg (from 1-a); Alltech C18 (25 cms 10 mm, 10 micron);
        Buffer A: 0.1% TFA
        Buffer B: 0.25% TFA/CH$_3$CN (4:6)
        60% B, isocratic; 3000 psig;
        3.0 ml/min.
        Injection: 10 mg/0.6 ml in buffer A
        235 nm (2.0 AUFS).
    (a) 24 mg
    (b) 7.3 mg
    Combine 2-a and 2-b, repurified on HPLC to give 15 mg pure peptide.
3. Partition Chromatography:
    Sample: 117 mg (from 1-A),  G-25 fine (2.5 × 55 cm)
    n-BuOH/HOAc/H$_2$O 4:1;5

Purification of Pmp—D-Tyr—Phe—Val—Asn—Cys—Pro—Arg

| | |
|---|---|
| (a) fr. 32-36 | 83 mg of pure product |

EXAMPLE 3

Preparation of

Pmp—D-Tyr(Et)—Phe—Val—Asn—Cys—Pro—Arg—$NH_2$

The titled compound was prepared by the solid phase method on benzhydrylamine resin (BHA). Thus, 1.0 g BHA resin (1.13 mmol $NH_2$/g resin) was reacted with 1.5 equivalents of Boc-Arg(Tos), 1.5 equivalents of DCC and 3.0 equivalents of HBT which were made up in dimethylformamide to be 0.1M in Boc-Arg(Tos). Deblocking was performed with 50% TFA/methylene chloride and neutralization with 5% DIEA/methylene chloride. The peptide was elongated, stepwise, by coupling, using preformed Boc aminoacyl symmetrical anhydrides in DMF (0.1M). Boc-Asn, Boc-D-Tyr(Et) and Pmp(MBz) were successively coupled using DCC and HBT in DMF. Completeness of coupling was monitored by the qualitative ninhydrin test and recoupling was performed as necessary. The completed Pmp(MBz)-D-Tyr(Et)-Phe-Val-Asn-Cys(MBz)-Pro-Arg(Tos)-BHA resin was washed with methylene chloride and dried to constant weight, 2.34 g.

The peptide was deblocked and cleaved from the resin by treatment with anhydrous liquid hydrogen fluoride (30 ml) in the presence of anisole (4 ml) at 0° for one hour. After evaporation to dryness under vacuum, the resin was washed with ethyl ether, air dried and, then, extracted with degassed dimethylformamide (3×20 ml) and 20% acetic acid (4×20 ml). The DMF and acid extracts were added to 4 l of water (pH 4.5 with acetic acid). The pH was adjusted to 7.2 with ammoniium hydroxide and the solution was titrated with 0.01M potassium ferricyanide under argon with stirring until a yellow color persisted (85 ml). The pH was brought to 4.8 with glacial acetic acid. The mixture was filtered and the filtrate passed over a Bio-Rex 70 column (H⊕). After washing the column with water (200 ml) the crude peptide was eluted with 300 ml of pyridine/acetic acid/water (30:4:66 v/v). The eluant was evaporated under vacuum at 30°. The residue was dissolved in 100 ml of 0.2N acetic acid, then, lyophilized, yielding 507 mg of the crude titled octapeptide.

Purification of

Pmp—D-Tyr(Et)—Phe—Val—Asn—Cys—Pro—Arg—$NH_2$

1. Counter-current distribution:
   Sample: 607 mg crude, n-BuOH:HOAc:$H_2O$, 4:1:5, 240 transfers
   (a) fr. 154-170 & 190-192    71 mg
   (b) fr. 171-189    230 mg
2. Gel filtration
   Sample: 123 mg of Sample (b), G-15 (2.5 × 55 cm) using 0.2 N HOAc, 25 ml/hr
   (a) fr. 46-50    ~20 mg Purification of Pmp—D-Tyr(Et)—Phe—Val—Asn—Cys—Pro—Arg—$NH_2$

| | |
|---|---|
| (b) fr. 51-77 | 60 mg pure peptide |

EXAMPLE 4

Preparation of

Pmp—D-Leu—Phe—Val—Asn—Cys—Pro—Arg—$NHC_3H_7$

A mixture of 0.1 mmole of ($Pmp^1$-$D$-$Leu^2$-$Val^4$-desGly$NH_2$)AVP, prepared as described above but using Boc-D-Leu at position 2, and 0.1 mmole of n-propylamine in 20 ml of DMF was reacted with 23 mg (0.11 mmol) of DCC and 14 mg (0.11 mmol) of HBT at room temperature for 2 hours. The volatiles were evaporated to give an oily product residue. The product was purified as described above using: (1) gel filtration over G-10-Sephadex eluted with 0.2N acetic acid; (2) high pressure liquid chromatography using 0.05% TFA in 39% acetonitrile in water; and, again, (3) gel filtration to give 20 mg of the pure octapeptide of the title.

Amino acid analysis: Asp 0.88, Pro 0.93, Val 1.00, Leu 1.09, Phe 0.88, Arg 1.07. HPLC=95% major peak at 11.33 with 40% aqueous acetonitrile with 0.05M $KH_2PO_4$ as buffer. $K_{bind}$=12.1% inhibition at $10^{-5}$M.

Using ($Pmp^1$-$D$-$Tyr(Et)^2$-$Val^4$-desGly$NH_2$)-AVP prepared as in Example 2 above and benzylamine gives Pmp—D-Tyr(Et)—Phe—Val—Asn—Cys—Pro—ArgNHBzl.

Other N-alkylated derivatives are prepared similarly.

EXAMPLE 5

Solid Phase Peptide Synthesis of Pmp(4-MeBzl)-D-Tyr(Et)-Phe-Abu-Asn-Cys(4-MeBzl)-Pro-Arg(Tos)-BHA resin For the solid phase synthesis of the titled resin-supported peptide, Boc-Arg(Tos)BHA resin (1.19 mmol/g of resin) was used as a starting material. It was prepared by reaching Boc-Arg(Tos), 3 mmol, with the benzhydrylamine resin, 1.0 mmol, in dimethylformamide for two hours. The benzhydrylamine resin as the hydrochloride salt was covered with methylene chloride overnight. It was, then, washed with methylene chloride (4×1 min), neutralized with 7% diisopropylethylamine in methylene chloride (2×2 min), then, 6×1 min with methylene chloride alone and, finally, 2×1 min with predried dimethylformamide. The loading of Boc-Arg(Tos) on the resin was carried out twice on the shaker using 1-hydroxybenzotriazole (HBT, 6 mmol) and dicyclohexylcarbodiimide (DCC, 3 mmol). A quantitative ninhydrin test and amino acid analysis were performed routinely after loading to determine the percentage loading on the resin. Loading in this particular run was 62.66%, i.e. 0.74 mmol/g of resin was available. The subsequent amino acid, Boc-Pro, was coupled on the shaker using the following protocol.

(1) Washed with methylene chloride (6 times, 1 min).
(2) Prewashed with 50% TFA in methylene chloride (1 time, 1 min).
(3) Deprotected with 50% TFA in methylene chloride (20 min).
(4) Washed with methylene chloride (6 times, 1 min).
(5) Prewashed with 7% DIEA in methylene chloride (1 time, 1 min).
(6) Neutralized with 7% DIEA in methylene chloride (8 min).
(7) Washed with methylene chloride (6 times, 1 min).
(8) Washed with dimethylformamide (2 times, 1 min).
(9) Added protected amino acid (3 mmol) and HBT, 6 mmol, in DMF, followed by the addition of DCC in methylene chloride, 3 mmol, and coupling for 2 hours.
(10) Washed with dimethylformamide (2 times, 1 min).
(11) Washed with methylene chloride (4 times, 1 min).
(12) Washed with ethanol/methylene chloride 1:1 (2 times, 1 min).
(13) Washed with methylene chloride (4 times, 1 min).

The subsequent amino acids were coupled sequentially using Beckman peptide synthesizer 990-B. The program used for each coupling except BocAsn and Pmp(4-MeBzl) was as follows.
(1) Washed with methylene chloride (3 times, 1 min).
(2) Prewashed with 50% TFA in methylene chloride (1 time, 1 min).
(3) Deprotection with 50% TFA in methylene chloride (30 min).
(4) Washed with methylene chloride (3 times, 1 min).
(5) Prewashed with 7% DIEA in methylene chloride (1 time, 1 min).
(6) Neutralized with 7% DIEA in methylene chloride (1 time, 10 min).
(7) Washed with methylene chloride (3 times, 1 min).
(8) Protected amino acids (3 mmol) in methylene chloride, followed by addition of DCC, 3 mmol, 10 ml of 0.3M in methylene chloride, and coupling for two hours.
(9) Washed with methylene chloride (3 times, 1 min).
(10) Washed with ethanol/methylene chloride, 1:1, (3 times, 1 min).
(11) Washed with methylene chloride (3 times, 1 min).

In case of coupling of Asn moiety, 1-hydroxybenzotriazole (HBT, 6 mmol) was used, 10 ml of 0.6M dimethylformamide. Dry dimethylformamide was also used as solvent when Pmp(4-MeBzl) was coupled onto the peptide resin, using 4-dimethylaminopyridine (3 mmol). Completion of each coupling reaction was monitored by the ninhydrin test. The 4-methylbenzyl (4-MeBzl) group was used to protect the thiol groups of the Cys and pentamethylene mercaptopropionic acid (Pmp) moieties.

Preparation of
Pmp-D-Tyr(Et)-Phe-Abu-Asn-Cys-Pro-ArgNH$_2$

Pmp(4-MeBzl)-D-Tyr(Et)-Phe-Abu-Asn-Cys-(4-MeBzl)-Pro-Arg(Tos)BHA-resin, 1.25 g, (0.37 mmol) in 2 ml of anisole, was reacted with anhydrous hydrogen fluoride (20 ml at 0° for 50 min). After evaporation of HF in vacuo, the residue was washed with anhydrous ether, 4×20 ml, and the crude peptide was extracted with dimethylformamide (50 ml) and 33% acetic acid (50 ml) into 2 liter of degassed water previously adjusted to pH 4.5. The aqueous diluted disulfhydryl octapeptide was cyclized using 0.01M potassium ferricyanide solution at pH 7.2 until the yellow color persisted for 30 minutes (50 ml). The pH was adjusted to 4.5 using glacial acetic acid and the solution was passed through a weakly acid acrylic resin (Bio-Rex-70) column (2.5×12, H$^\oplus$ form), slowly. The column was eluted with pyridine-acetate buffer (30:4:66; pyridine/glacial acetic acid/water). The pyridine acetate solution was removed by distillation in vacuo. The residue was lyophilized from 10% acetic acid to give 300 mg (76%) of crude titled peptide.

Purification of

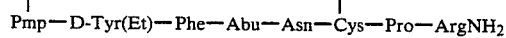

| 1. | Counter-current distribution: | |
|---|---|---|
| | Sample: 300 mg, n-BuOH/HOAc/H$_2$O, 4:1:5, 240 transfers. | |
| | (a) fr. 176–186, 99.6 mg of pure peptide | |
| | (b) fr. 170–175 and 187–210, 117.24 mg | |
| | Yield of purified material, 216.84 mg (55%) | |
| 2. | Molecular Formula: | C$_{50}$H$_{72}$N$_{12}$O$_{10}$S$_2$ |
| | Molecular Weight: | 1064.53 |
| | Amino Acid Analysis: | Asp (1.00), Abu + Cys (1.70), Tyr (0.64), Phe (0.98), Arg (0.91) |
| | Peptide Content: | 68.06–91.52% from amino acid analysis 87.33% from nitrogen analysis |
| 3. | Chromatography Data: | Solvent | R$_f$ |
| | TLC | n-BuOH/HOAc/H$_2$O/EtOAc (1:1:1:1) | 0.56 |
| | | n-BuOH/HOAc/H$_2$O/ (4:1:5) Upper | 0.42 |
| | HPLC Isocratic | C$_{18}$-column H$_2$O/CH$_3$CN/TFA, (60:40:0.25) | k′ 3 |
| | | 0.05 MKH$_2$PO$_4$: acetonitrile (60:40) | 7.33 |
| | Gradient | H$_2$O/CH$_3$CN/TFA, 80:20:0.25 to 50:50:0.25 | 8.82 |
| | Fast Atom Bombardment (FAB): | m/z 1065 (M + H)$^+$; 1063 (M − H)$^-$ | |

EXAMPLE 6

Solid Phase Peptide Synthesis of
Pmp-(4-MeBzl)-D-Tyr(Et)-Phe-Ala-Asn-Cys-4-MeBzl)-Pro-Arg(Tos)-BHA resin The tetrapeptide supported resin, Boc-Asn-Cys(4-MeBzl)-Pro-Arg(Tos)-BHA, 0.72 g (0.36 mmol), was synthesized on Beckman 990-B peptide synthesizer, starting from the Boc-Arg(Tos) benzhydrylamine resin (0.72 mmol/g) using a protocol like that of Example 5. The subsequent amino acids were coupled sequentially on the shaker using HBT and DCC for 2 hours in a similar fashion. After coupling of the last residue, i.e, Pmp(4-MeBzl), the resin containing peptide was washed as usual, dried to give 0.88 g of the titled intermediate.

Preparation of

Pmp(4-MeBzl)-D-Tyr(Et)-Phe-Ala-Asn-Cys(4-MeBzl)-Pro-Arg(Tos)-BHA-resin, in 2 ml of anisole, was reacted with anhydrous HF, 20 ml, at 0° for 50 minutes. The work up was done as usual and the uptake of $K_3Fe(CN)_6$ was 45 ml to give 230 mg (60.8%) of crude titled peptide.

Purification of

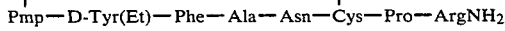
Pmp—D-Tyr(Et)—Phe—Ala—Asn—Cys—Pro—ArgNH$_2$

1. Counter-current distribution:
   Sample: 230 mg, n-BuOH/HOAc/H$_2$O, 4:1:5, 240 transfers
   (a) fr. 160-178, 105.2 mg pure product
   (b) fr. 179-190 and 150-159, 49.5 mg
   Yield of purified material, 154.7 mg (41%).
2. Molecular Formula: $C_{49}H_{70}N_{70}O_{10}S_2$
   Molecular Weight: 1050.449
   Amino Acid Analysis: Asp (1.00), Pro (1.03), Ala (0.94), Cys (0.46), Tyr (0.65), Phe (0.91), Arg (0.92).
   Peptide Content: 59.18–81.77% from two analyses.
3. Chromatography Data:

| | Solvent | $R_f$ |
|---|---|---|
| TLC | mBuOH/HOAc/H$_2$O/EtOAc (1:1:1:1) | 0.64 |
| HPLC | $C_{18}$-column | k' |
| Isocratic | H$_2$O/CH$_3$CN/TFA, 60:40:0.1 | 2.18 |
| Gradient | H$_2$O/CH$_3$CN/TFA, 60:40:0.1 to 50:50:0.1 | 6.47 |
| Fast Atom Bombardment (FAB): | m/z 1051 (M + H)$^+$; 1049 (M − H)$^-$ | |

EXAMPLE 7

Solid Phase Peptide Synthesis of Pmp(4-MeBzl)-D-Tyr(Et)-Phe(4'-Et)-Val-Asn-Cys-(4-MeBzl)-Pro-Arg(Tos)-BHA-resin The titled resin-supported peptide was prepared from BOC-Arg(Tos) BHA resin (0.4 mmol/g) on a shaker using a protocol used before i.e. deprotection-coupling using HBT and DCC for 2 hours, up to Boc-Val-Asn-Cys-(4-MeBzl)-Pro-Arg(Tos)-BHA resin. The next two amino acid residues were coupled using the Beckman peptide synthesizer 990-B. The Pmp(4-MeBzl) was coupled manually using DMAP-DCC overnight. The resin-containing peptide was washed and dried as usual to give 2.00 g of the titled intermediate.

Preparation of

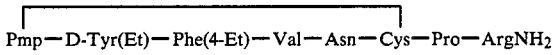
Pmp—D-Tyr(Et)—Phe(4-Et)—Val—Asn—Cys—Pro—ArgNH$_2$

Pmp-(4-MeBzl)-D-Tyr(Et)-Phe(4-Et)-Val-Asn-Cys-4-MeBzl)-Pro-Arg(Tos)-BHA resin, in 3 ml of anisole was reacte with 30 ml of anhydrous hydrogen fluoride at 0° for an hour. The work up was done as described above, with 38 ml of K$_3$Fe(CN)$_6$ taken up. About 50 mg of crude peptide was obtained from the Bio-Rex column and 139 mg was precipitated out of solution, total yield 189 mg (42.7%) of titled peptide.

Purification:
1. Partition column chromatography, Sephadex, G-25:
   Sample: 50 mg, n-BuOH/HOAc/H$_2$O, 4:1:5,
   (a) fr. A, 23.86 mg
   (b) fr. B, 18.5 mg
   Preparative HPLC
   Sample: 43 mg (From 1, Fr. a + Fr. b), Altex ODS, 10 mm × 25 cm, 5μ, flow rate 4 ml/min.,
   water/acetonitrile/TFA (50:50:0.25), isocratic, 229 nm (2.0 AUFS), injection 2.0 mg/300 μl and 4.0 mg/420 ml to give 30.0 mg of pure peptide.
2. Physical Data:
   Molecular Formula: $C_{53}H_{78}N_{12}O_{10}S_2$
   Molecular Weight: 1106.47
   Amino Acid Analysis: Asp (1.00), Pro (0.78–0.84), Cys (0.45), Val (1.02), Tyr (0.63), Phe (p-Et) (1.50), Arg (1.00–0.96)
   Peptide Content: 73.3–89.6%
3. Chromatography Data:

| | Solvent | $R_f$ |
|---|---|---|
| TLC | nBuOH/HOAc/H$_2$O/EtOAc, 1:1:1:1 | 0.70 |
| | nBuOH/HOAc/H$_2$O, 4:1:5 Upper | 0.299 |
| HPLC | $C_{18}$ Column | k' |
| Isocratic | H$_2$O/CH$_3$CH/TFA, 55:45:0.1 | 4.43 |
| Gradient | H$_2$O/CH$_3$CN/TFA, 60:40:0.1 to 50:50:0.1 | 8.7 |
| FAB | m/z 1107 (M + H)$^+$; 1105 (M + H)$^-$ | |

EXAMPLE 8

Synthesis of Boc-Asn-Cys(4-MeBzl)-Pro-Arg(Tos)MBHA resin

One millimole of Boc-Asn-Cys(4-MeBzl)-Pro-Arg(Tos)-BHA resin was prepared using 1 mmole of Boc-Arg(Tos)-4-methylbenzhydrylamine (MBHA) resin as starting material by coupling sequentially with the appropriate t-Boc-protected amino acids in a Beckman 990-B peptide synthesizer, 990-B.

1.83 Grams of the protected peptide resin was obtained and was divided into two equal parts of 0.915 g each.

Synthesis of

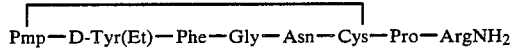
Pmp—D-Tyr(Et)—Phe—Gly—Asn—Cys—Pro—ArgNH$_2$

One part of the protected peptide resin from above was further sequentially coupled with 1.5 mmoles of the appropriate Boc amino acids and β-(S-MeBzl)-Pmp-OH to give 1.16 g of the final protected peptide resin. Pmp(S-MeBzl)-D-Tyr(Et)-Phe-Gly-Asn-Cys(4MeBzl)-Pro-Arg(Tos)MBHA resin was obtained and dried in vacuo. This protected resin was treated with 1.5 ml of anisole and 25 ml of anhydrous hydrogen fluoride at 0° for 1 hour. The deprotected peptide was treated with 0.01 mole of potassium ferricyanide solution at pH 7.2 in 2 liters of water. 53 Ml of the oxidizing agent was used.

The resulting solution was passed through a $C_{18}$ flash column. The column was eluted with 50% of acetonitrile with 0.25% trifluoroacetic acid in 20 ml per fraction. 325 Mg crude product was isolated from the fractions. Further purification of the product by CCD (B/A/W, 4:1:5) to obtain 188 mg of 99% pure titled product.

| Amino acid analysis: | |
|---|---|
| Peptide content | 82% |
| Asp 1.04 | Tyr 0.92 |
| Pro 1.15 | Phe 1.01 |
| Gly 1.00 | Arg 0.91 |

-continued

| Amino acid analysis: |
| --- |
| Cys 0.54 |

FAB/MS = m/z (M + H)+ 1037

EXAMPLE 9

Synthesis of

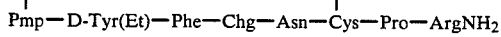
Pmp—D-Tyr(Et)—Phe—Chg—Asn—Cys—Pro—ArgNH$_2$

One part of the protected peptide resin from Example 8 was further sequentially coupled with 1.5 mmoles of the appropriate Boc amino acids and β-(S-4-MeBzl)-Pmp-OH to give 1.06 g of the final protected peptide resin, Pmp(S-4-MeBzl)-D-Tyr(Et)-Phe-Chg-Asn-Cys(S-4-MeBzl)-Pro-Arg(Tos)MBHA resin, obtained after drying in vacuo.

This protected peptide resin was treated with 1.5 ml of anisole and 25 ml of anhydrous hydrogen fluoride.

Following the usual oxidation by potassium ferricyanide and isolation over a C$_{18}$ column, 165 mg crude titled product was obtained. Further purification by CCD G-15 and P-2 gel filtration as described above gave 55 mg HPLC pure titled product.

Peptide content: 88%

FAB/MS: m/z 1119 (M+H)+

EXAMPLE 10

Preparation of Pmp—D-Tyr(Et)—Phe—Val—Asn—Cys(OH) and its use for preparing the compound of Example 3.

4.87 g (15 mmol) of the BocCys(4MeBzl) was dissolved in 30 ml of ethanol and 10 ml of water added. The pH was then adjusted to 7.1 with an aqueous solution of cesium bicarbonate.

The mixture was concentrated and the residue evaporated three times from 50 ml of toluene. This residue was, then, placed under high vacuum at ambient temperature overnight.

The salt was dissolved in 35 ml of dimethylformamide and 5 g of commercial chloromethylphenyl resin added. The mixture was stirred at 53° under argon overnight.

The mixture was filtered and the resin washed with dimethylformamide (5×60 ml), DMF/Water, 9:1 (5×60 ml), DMF (5×60 ml) and ethanol (6×60 ml). It was, then, dried under high vacuum at ambient temperature over the weekend.

The peptide chain was built up in a Beckman synthesizer as described above using the Boc derivatives of Asn, Val, Phe, D-Tyr(Et) and the S-(4-MeBzl) Pmp derivative. The resin was removed and placed in a manual shaker.

0.86 G of the peptide resin was treated with 1.5 ml of anisole and stirred for 60 min at 0° in 15 ml of hydrogen fluoride. The hydrogen fluoride was, then, removed under aspirator pressure at 0°.

The residue was then washed with 3×25 ml of ether (discarded) and the peptide eluted with dimethylformamide and 30% acetic acid (4×10 ml). This solution was added to 2 l of degassed water and the pH adjusted to 7.0 with ammonium hydroxide. A 0.01M potassium ferricyanide solution was added slowly (35 ml).

The pH was then adjusted to 4.5 with acetic acid and the mixture stirred for 30 minutes with 25 g (WET) of a weakly basic ion exchange resin (AG-3×4 1R-4S). The suspension was filtered and the resin washed with 2×400 ml of 30% acetic acid.

The filtrate was, then, passed thru a C$_{18}$ flash column (7×16 mm). The column was then washed with water (3×400 ml) and the peptide eluted with acetonitrile/water/TFA, 50:50:0.25). Fractions 30→36 were combined, concentrated and lyophilized to yield 25 mg of the titled free Cys(OH)cyclic intermediate.

FAB mass spectrum in glycerol: 827 (M+H)+, 825 (M−H)−.

The Cys acid (20 mg) is reacted with one equivalent of Pro-Arg(NH$_2$)HCl (prepared from the commercial dihydrochloride by treatment with 1 equivalent of triethylamine) in the presence of DCC and HBT in dimethylformamide to produce the compound of Example 3. Similarly, Pro(OMe) is attached to the Cys acid, hydrolyzed with mild sodium hydroxide to give the Pro acid which is, then, reacted with Arg(HCl)(OMe) to give the acid parent of the compound of Example 3 after mild hydrolysis of the ester. This compound is isolated as the potassium salt if desired. See Example 12 below. Alternatively, the Pro-Arg(NH$_2$) is used in the condensation directly.

A mixture of 4.5 mg of Pmp-D-Tyr(Et)-Phe-Val-Asn-Cys-OH prepared as above and 1 ml of methanol was treated with ethereal diazomethane and purified by preparing HPLC (50% CH$_3$CN/50% H$_2$O/0.1% TFA) to yield 4.3 mg of the methyl ester (94%), FABMS m/z 841 (M+H)+, homogeneous by HPLC and TLC.

EXAMPLE 11

Preparation of

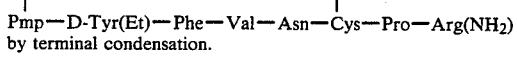
Pmp—D-Tyr(Et)—Phe—Val—Asn—Cys—Pro—Arg(NH$_2$)
by terminal condensation.

BocPro-Merrifield resin was made by coupling Boc-Pro to Merrifield resin using the cesium salt method to give Boc-Pro-OCH$_2$-C$_6$H$_4$-resin which was used as the starting material for the synthesis. The synthesis was carried out on the Beckman 990-B peptide synthesizer using the following protocol. Three equivalents of the amino acids were dissolved in their appropriate solvents [the Boc derivatives of 4MeBzl-Cys, Val, Phe in methylene chloride, Asn in dimethylformamide, X such as D-Tyr(Et) or BrBz-D-Tyr in 1:1 methylene chloride/dimethylformamide and 4MeBzl-Pmp in methylene chloride] and were coupled using an equimolar amount of dicyclohexylcarbodiimide (DCC) and 1-hydroxybenzotriazole (HOBT) except for the coupling of 4MeBzl Pmp where 1.0 equivalent of dimethylaminopyridine was used as catalyst. The extent of coupling was determined by qualitative ninhydrin analyses and couplings were repeated when necessary. The Boc groups were removed using 1:1 trifluoroacetic acid/methylene chloride and after washing the free amine was generated using 5% diisopropylethylamine/methylene chloride. The sequence of the peptide was checked using solid phase sequencing befor the coupling of the 4MeBzl-Pmp and its homogeneity confirmed. After the final coupling, the resin was dried to give 2.24 g of peptide resin in the case of the D-Tyr(Et)$^2$-Pro$^7$ compound.

1.1 G (0.5 mmole) of the D-Tyr(Et)$^2$ peptide resin with 3 ml of anisole was stirred 60 min. at 0° (ice bath)

in 25 ml of hydrogen fluoride (HF). The HF was, then, removed under reduced pressure at 0°. The residue was washed with ethyl ether (4×20 ml, discarded) and the peptide eluted with dimethylformamide 3×10 ml, 20% acetic acid 3×10 ml and 0.3N ammonium hydroxide 3×10 ml.

The filtrate was added to 2 l of degassed water and the pH adjusted to 7.1 with conc. ammonium hydroxide. A 0.01M solution of potassium ferricyanide was then added dropwise with stirring until a faint yellow color persisted (41 ml). This solution was adjusted to pH=4.7 with acetic acid and stored in the cold overnight.

The solution was adjusted to pH=7 with ammonia and stirred for 15 min with 30 g of AG-3×4 Bio-Rad ion exchange resin (wet, Cl form). This solution was then filtered slowly through an additional 30 g of resin. The resin was then washed with 4×200 ml of 20% acetic acid and the filtrate stored in the cold overnight.

The filtrate was then passed through a flash column (5 cm×10 cm) of a packing of silica gel coated with a C-18 silane. The column was then, washed with 350 ml of water and the peptide eluted with 500 ml of 1:1 acetonitrile/water (0.25% trifluoroacetic acid) in 20 ml fractions.

Fractions 11-17 were combined and concentrated. The residue was dissolved in conc. acetic acid, diluted with water and lyophilized to yield 189 mg of the D-Tyr(Et)[2], proline peptide, which was used without further purification for the synthesis of the tail modified peptides.

---

Identification of:

Pmp—D-Tyr(Et)—Phe—Val—Asn—Cys—Pro(OH)

| Amino Acid Analysis: | Peptide Content 55% |
|---|---|
| | Asp, 1.00; Pro, 1.23; Cys, 0.35; Val; 1.04, Tyr(Et), 1.43; Phe, 1.51. |
| HPLC: | Satisfactory. |

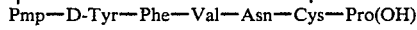
Pmp—D-Tyr—Phe—Val—Asn—Cys—Pro(OH)

| Amino Acid Analysis: | Peptide Content 82% |
|---|---|
| | Asp, 0.97; Pro, 1.10; Cys, 0.39; Val, 1.05; Tyr, 0.99; Phe, 0.99 |
| HPLC: | Satisfactory, 30% CH$_3$CN/70% 0.05 m KH$_2$PO$_4$, 2 ml/min, 5 uC-18, k' = 6.14. |

---

A mixture of 10 mg of the D-Tyr(Et)-Pro(OH)[7] prepared as above, and 1 ml of methanol was treated with ethereal diazomethane and, then, purified by preparing HPLC (50% CH$_3$CN/50% H$_2$O/0.1% TFA) to yield 7.5 mg of the methyl ester (74%), FABMS m/z 938 (M+H+), homogeneous by HPLC and TLC.

To a solution of the D-Tyr(Et)[2]-proline heptapeptide, prepared as described above, (29.7 mg, 0.0331 mmol), and Arg(NH$_2$) (0.0996 mmol) in dimethylformamide (400 μl), dicyclohexylcarbodiimide (10.3 mg, 0.05 mmol) and dimethylaminopyridine (0.05 mmol) were added and the reaction mixture was stirred at 0°-20° for 4 hours. The dimethylformamide was, then, removed under vacuum. The residue was treated as above in Example 3 in 45% yield to give the desired D-Tyr(Et)[2]-Val[4] amide.

EXAMPLE 12

Synthesis and Characterization of

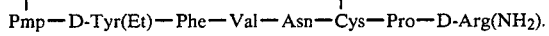
Pmp—D-Tyr(Et)—Phe—Val—Asn—Cys—Pro—D-Arg(NH$_2$).

The linear peptidyl resin, Pmp(S-MeBzl)-D-Tyr(Et)-Phe-Val-Asn-Cys(S-MeBzl)-Pro-D-Arg(Tos)-BHA resin, was prepared by the solid phase method using the standard protocol described above. Thus, 1.5 g benzhydrylamine resin corresponding to 1.0 mmol amine was coupled successively with the Boc amino acid derivatives in threefold excess using DCC/HOBt in methylene chloride/DMF, 1:1. Pmp(S-MeBzl) was coupled with DCC/DMAP. Completeness of coupling was checked with the Kaiser test or a quantitative ninhydrin test. Recoupling was performed until the test was negative.

The protected peptidyl resin was washed with successive portions of methylene chloride, methanol, ethyl acetate and methylene chloride, and, then, air dried. The peptide was cleaved from the resin with 15 ml of liquid hydrogen fluoride in the presence of 1.0 ml of anisole at 0° for one hour. After evaporation of the hydrogen fluoride and drying under high vacuum, the resin was washed with 3×20 ml of ether and, then, extracted with 2×50 ml of 50% acetic acid, 50 ml of 10% acetic acid, and 50 ml of water. The combined extracts were diluted to 4 l with water and the pH adjusted to 7.2 with 50% sodium hydroxide solution. The solution was titrated with 0.01M K$_3$Fe(CN)$_6$ solution until a yellow color persisted (30 ml). The pH was adjusted to 4.5 with glacial acetic acid and filtered. The filtrate was applied to a cation exchange (BioRex-70) column (H+ form), washed with water and then eluted with 100 ml of pyridine acetate buffer (30 ml of pyridine, 4 ml of acetic acid, 66 ml of water). The eluant was evaporated to dryness. The residue was dissolved in a small amount of 10% acetic acid and diluted with water to 1% acetic acid, then lyophilized, yielding 650 mg of the crude titled peptide.

The crude peptide was purified by counter current distribution in n-butanol/acetic acid/water (B/A/W) (4:1:5) yielding 33 mg partially purified peptide. This was further purified by gel filtration on a Sephadex G-15 column in 1% acetic acid, yielding 24.5 mg pure peptide. Amino acid analysis (hydrolysis in HCl/TFA 2:1, 0.005% phenol for 1 hr.) Asp 1.00, Pro 0.72, Cys 0.62, Val 0.99, Tyr 1.04, Phe 1.04, Arg 0.95, 71% peptide. HPLC: (40% acetonitrile/60% water/0.1% TFA), one peak, k'=5.2; (45% acetonitrile/55% water/0.1% TFA) k'=3.6; (gradient 20% acetonitrile, 5'; 20-50% acetonitrile, 20'; 50% acetonitrile, 5') k'=8.7, 97% pure. Tlc: rf 0.32 (B/A/W 1:1:1); 0.12 (B/A/W 4:1:1); 0.50 (n-butanol/pyridine/acetic acid/water), 15:10:3:12).

The extracted peptidyl resin still contained peptide by amino acid analysis, so it was extracted with 3×50 ml of DMF. The DMF was evaporated to dryness and the residue dissolved in 10% HOAc, diluted to 1% acetic acid and lyophilized, yielding an additional 260 mg of peptide. FAB mass spectrometry of this material gave a m/z 1079 which corresponds to M+H for the desired cyclic peptide.

EXAMPLE 13

Substituting a stoichiometric quantity of Boc-D-Phe for Boc-D-Tyr(Br-Z) at the 2 unit of the peptide synthesis of Example 1 gives

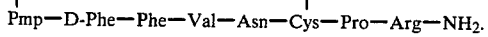
Pmp—D-Phe—Phe—Val—Asn—Cys—Pro—Arg—NH$_2$.

Substituting Boc-D-Val at the same position using the splitting-oxidation reactions of Example 2 gives

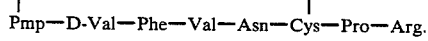
Pmp—D-Val—Phe—Val—Asn—Cys—Pro—Arg.

Substituting Boc-D-Leu in Example 1 gives

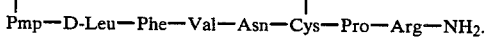
Pmp—D-Leu—Phe—Val—Asn—Cys—Pro—Arg—NH$_2$.

Substituting β-mercapto-β,β-cyclotetramethylenepropionic acid (Tmp) for Pmp in Example 5 gives

Tmp—D-Tyr(Et)—Phe—Abu—Cys—Pro—Arg(NH$_2$).

β-Mercapto-β,β-cyclohexamethylenepropionic acid gives the Hmp$^1$ derivative.

Substituting in Example 1 Boc-D-Nle at the 2 unit and D-Arg(Tos) at the 8 unit gives

Pmp—D-Nle—Phe—Val—Asn—Cys—Pro—D-Arg—NH$_2$.

Substituting in Example 2 Boc-D-Cha at the 2 unit gives

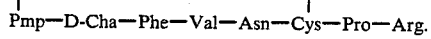
Pmp—D-Cha—Phe—Val—Asn—Cys—Pro—Arg.

Substituting in Example 1 Boc-α-aminophenylbutyric acid (Pba) at the 2 unit gives

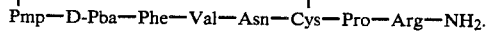
Pmp—D-Pba—Phe—Val—Asn—Cys—Pro—Arg—NH$_2$.

Substituting Boc-Lys(ClZ) in Example 3 for the protected Arg gives

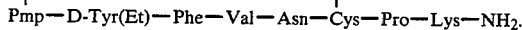
Pmp—D-Tyr(Et)—Phe—Val—Asn—Cys—Pro—Lys—NH$_2$.

Other representative compounds which are prepared in like manner are:

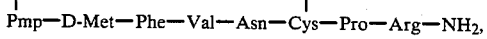
Pmp—D-Met—Phe—Val—Asn—Cys—Pro—Arg—NH$_2$,

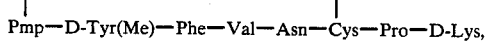
Pmp—D-Tyr(Me)—Phe—Val—Asn—Cys—Pro—D-Lys,

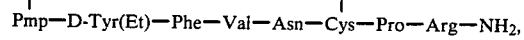
Pmp—D-Tyr(Et)—Phe—Val—Asn—Cys—Pro—Arg—NH$_2$,

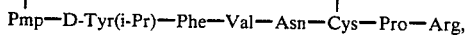
Pmp—D-Tyr(i-Pr)—Phe—Val—Asn—Cys—Pro—Arg,

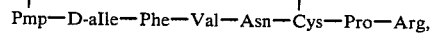
Pmp—D-aIle—Phe—Val—Asn—Cys—Pro—Arg,

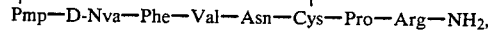
Pmp—D-Nva—Phe—Val—Asn—Cys—Pro—Arg—NH$_2$,

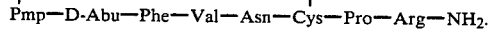
Pmp—D-Abu—Phe—Val—Asn—Cys—Pro—Arg—NH$_2$.

EXAMPLE 14

Parenteral Dosage Unit Compositions

A preparation which contains 0.5 mg of the cyclic octapeptide of Examples 1 or 3 as a sterile dry powder for parenteral injection is prepared as follows: 0.5 mg of peptide amide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from edema susceptible to anti-ADH mechanism of action. The injection is repeated as necessary, from 1–5 times daily or in continuous i.v. drug injection. Other octapeptides of this invention are made up and used in like manner.

Nasal Dosage unit Compositions

30 Mg of finely ground octapeptide of this invention such as the product of Example 2 is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to an edematous subject from 1–6 times a day.

What is claimed is:

1. A polypeptide compound of the formula:

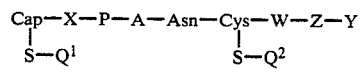
Cap—X—P—A—Asn—Cys—W—Z—Y
   |                    |
   S—Q$^1$              S—Q$^2$ in which:

X is D-Phe, D-Val, D-Leu, D-Ile, D-Nva, D-Pba, D-Nle, D-Cha, D-Abu, D-Met, D-Chg, D-Tyr, L-Tyr, D-aIle, D-Tyr(alk) or L-Tyr(alk);

P is Phe or Phe(4'Alk);

Y is NH$_2$, NHAlk, NHBzl or OH;

A is Val, Ile, Abu, Ala, Gly, Lys, Cha, Nle, Phe, Leu, Chg or Nva;

W is L-Pro, ΔPro, D-Pro or, when Y is OH, a single bond;

Z is D-Arg, L-Arg, D-Lys, L-Lys or, when Y is OH, a single bond;

Q$^1$ and Q$^2$ are both a displaceable group; and

Cap is a β,β-cycloalkylene propionic acid with S-Q$^1$ attached at the β-position and having 5–7 units in the cycloalkylene chain, or ester derivatives thereof.

2. The compound of claim 1 in which $Q^1$ and $Q^2$ are acetamidomethyl.

3. The compound of claim 1 in which $Q^1$ and $Q^2$ are acetamidomethyl, Y is OH and Z is a single bond.

4. The compound of claim 1 being S-ACM-Pmp-D-Tyr(Et)-Phe-Val-Asn-S-ACM-Cys-Pro-OBzl.

5. The compound of claim 1 being S-Acm-Pmp-D-Tyr(Et)-Phe-Val-Asn-S-ACM-Cys-Pro(OH).

* * * * *